US011147760B2

(12) United States Patent
Argembeaux et al.

(10) Patent No.: US 11,147,760 B2
(45) Date of Patent: Oct. 19, 2021

(54) OIL-BASED EXFOLIATING CLEANSING PRODUCT

(71) Applicant: BEIERSDORF AG, Hamburg (DE)

(72) Inventors: Horst Argembeaux, Wendorf (DE); Anke Hoff, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 484 days.

(21) Appl. No.: 15/521,787

(22) PCT Filed: Aug. 25, 2015

(86) PCT No.: PCT/EP2015/069386
§ 371 (c)(1),
(2) Date: Apr. 25, 2017

(87) PCT Pub. No.: WO2016/066299
PCT Pub. Date: May 6, 2016

(65) Prior Publication Data
US 2017/0246103 A1 Aug. 31, 2017

(30) Foreign Application Priority Data

Oct. 29, 2014 (DE) .................. 102014222014.9

(51) Int. Cl.
| | | |
|---|---|---|
| *A61K 8/92* | (2006.01) | |
| *A61K 8/42* | (2006.01) | |
| *A61K 8/46* | (2006.01) | |
| *A61Q 19/10* | (2006.01) | |
| *A61K 8/81* | (2006.01) | |
| *A61K 8/02* | (2006.01) | |
| *A61K 8/41* | (2006.01) | |
| *A61K 8/20* | (2006.01) | |
| *A61K 8/34* | (2006.01) | |
| *A61K 8/60* | (2006.01) | |
| *A61Q 19/00* | (2006.01) | |

(52) U.S. Cl.
CPC ............ *A61K 8/922* (2013.01); *A61K 8/0241* (2013.01); *A61K 8/20* (2013.01); *A61K 8/345* (2013.01); *A61K 8/41* (2013.01); *A61K 8/42* (2013.01); *A61K 8/463* (2013.01); *A61K 8/60* (2013.01); *A61K 8/8152* (2013.01); *A61K 8/8182* (2013.01); *A61Q 19/00* (2013.01); *A61Q 19/10* (2013.01); *A61K 2800/28* (2013.01); *A61K 2800/5424* (2013.01); *A61K 2800/596* (2013.01)

(58) Field of Classification Search
CPC ........ A61K 2800/28; A61K 2800/5424; A61K 2800/596; A61K 8/20; A61K 8/345; A61K 8/42; A61K 8/463; A61K 8/60; A61K 8/8182; A61K 8/922; A61Q 19/00; A61Q 19/10
See application file for complete search history.

(56) References Cited

U.S. PATENT DOCUMENTS

| | | | |
|---|---|---|---|
| 4,371,548 A | 2/1983 | Hermann et al. | |
| 4,631,295 A | 12/1986 | Engel et al. | |
| 5,653,988 A | 8/1997 | Gerber et al. | |
| 6,132,738 A | 10/2000 | Lerg et al. | |
| 8,563,492 B2 | 10/2013 | Stolz et al. | |
| 2011/0046034 A1 | 2/2011 | Stolz et al. | |
| 2013/0039961 A1* | 2/2013 | Gonzales | A61K 8/8117 424/401 |
| 2016/0067152 A1* | 3/2016 | Franklin | A61K 8/8147 424/401 |
| 2018/0134991 A1* | 5/2018 | Sears | C11D 1/523 |

FOREIGN PATENT DOCUMENTS

| | | |
|---|---|---|
| DE | 2943202 A1 | 3/1981 |
| DE | 236014 A1 | 5/1986 |
| DE | 4424210 A1 | 1/1996 |
| DE | 19712678 A1 | 10/1998 |
| DE | 102013224336 A1 | 6/2014 |
| DE | 102013224368 A1 | 6/2014 |
| EP | 120224 A2 | 10/1984 |
| EP | 867176 A2 | 9/1998 |
| EP | 1967173 A1 | 9/2008 |
| WO | 03051319 A1 | 6/2003 |
| WO | 2005065629 A2 | 7/2005 |
| WO | 2012104025 A1 | 8/2012 |
| WO | 2014190989 A1 | 12/2014 |

OTHER PUBLICATIONS

National Center for Biotechnology Information. PubChem Database. Cocamidopropyl betaine, CID=20280, https://pubchem.ncbi.nlm.nih.gov/compound/Cocamidopropyl-betaine (accessed on Oct. 30, 2019). (Year: 2019).*
Mintel Database (Honey Sugar Mask) Published Apr. 2013 Record ID 2034019.†
Mintel Database (Sugar Body Scrub) Publication date Oct. 2013 Record ID 2197797.†
Mintel Database (Tommy Girl Sugar Scrub) Published Nov. 2001 Record ID 10097387.†

* cited by examiner
† cited by third party

*Primary Examiner* — Michael B. Pallay
(74) *Attorney, Agent, or Firm* — Abel Schillinger, LLP (57) ABSTRACT

The invention relates to an oil-based cleansing product which contains abrasive particles as exfoliating substances. In one particular embodiment, salt and sugar crystals are used as exfoliating substances.

20 Claims, 9 Drawing Sheets

After drying:

The consensus with regard to the gentle removal of dead skin cells is at a very good level.

| Test product | TOP 2 (6-7) in % | LOW 2 (1-2) in % |
|---|---|---|
| OELPEEL:70 | 77 | 4 |

The product gently removes dead skin cells.

Figure 4:

After drying:

The consensus with regard to a smooth skin feel after use is at a very good level.

| Test product | TOP 2 (6-7) in % | LOW 2 (1-2) in % |
|---|---|---|
| OELPEEL:70 | 78 | 4 |

The product ensures a smooth skin feel.

Figure 5:

After drying:

The volunteers are of the opinion that the product leaves a soft skin feel.

| Test product | TOP 2 (6-7) in % | LOW 2 (1-2) in % |
|---|---|---|
| OELPEEL:70 | 75 | 4 |

The product leaves a soft skin feel.

After 12 days use:

The statement that the skin does not tighten after 12 days' use is agreed with at a good level.

| Test product | TOP 2 (6-7) in % | LOW 2 (1-2) in % |
|---|---|---|
| OELPEEL:70 | 67 | 5 |

My skin does not tighten.

Figure 9:

After 12 days' use:

The moisturization of the skin is also classified at a good level.

| Test product | TOP 2 (6-7) in % | LOW 2 (1-2) in % |
|---|---|---|
| OELPEEL:70 | 52 | 8 |

My skin is adequately moisturized.

OIL-BASED EXFOLIATING CLEANSING PRODUCT

BACKGROUND OF THE INVENTION

1. Field of the Invention

The present invention describes oil-based cleansing products comprising abrasive particles, in a particular embodiment crystals of salt and/or sugar, as exfoliating substances.

The oils according to the invention are lipids, which may be either fats, which are solid or semi-solid at 20° C., or oils which are liquid. Native oils and fats are chemically largely triacylglycerols of higher fatty acids with an even number of carbon atoms. Petrochemical oils or fats are generally longer-chain, more or less branched or crosslinked, saturated or unsaturated or partially saturated hydrocarbons and derivatives thereof.

In the broader sense, the term lipid is understood to mean a certain group of biomolecules, which are structurally not at all uniform in nature, which is wholly or at least largely insoluble in water.

Lipids in the context of the present invention can be any desired oils and/or fats of the form described. Preference is given here to mixtures of lipids which are liquid and solid at room temperature.

Cleansing products, which comprise an enhanced oil or lipid content, have been on the market for a long time. The oil in the cleansing product is intended to be applied to the skin and to protect the skin, to normalize the skin condition and to contribute to the regeneration of damaged, sensitive or even aged skin.

In order to explain the protective function of lipids, the following proposal has been developed: the surfactants, in particular anionic surfactants, can adsorb and exert their effect on the upper skin layer. On the one hand, they remove dirt particles or a dirt film from the skin. However, on the other hand, not only the soil is removed but the skin's own lipids and natural moisturizing factors (NMF) are also removed. Since the oil components in the cleansing products can form a film on the skin, it is conceivable that the effect of the surfactants on the skin's own lipids and the natural moisturizing factors is limited.

In addition, the lipid film causes the skin not to dry out as much and contributes to the regeneration of the skin's own lipid film via the refatting process.

Damaged skin, sensitive skin or aged skin is often characterized by being dry. In the case of the use of conventional cleansing products which contain no oil or only very little oil, a further impairment of the skin is caused by the removal of the skin's own lipids and natural moisturizing factors. The skin dries out even further. There may be a feeling of tension in the skin, redness and itching. It is precisely for users with such skin conditions that oil-based cleansing preparations are able to provide a remedy.

2. Discussion of Background Information

In the prior art, oil-based cleansing preparations have been disclosed for some time.

Document DE 29 43 202 describes compositions having a cleansing and skin-care effect and are based on mixtures of surfactants and oils, which are preferably used as so-called soothing foam baths, although the use of these compositions as shower preparation is also mentioned. The preparations described have a content of 20 to 80% by weight of an aqueous surfactant solution, which consists in turn of 85 to 95% by weight surfactant and 5 to 15% by weight water, and an oil content of 80 to 20% by weight. The detersive component of these preparations consists of mono- or dialkylamine, mono- or dialkanolamine or alkylalkanolamine salts of fatty alcohol sulfuric acid esters.

EP 120 224 describes active ingredient-containing oil bath preparations containing 38.75% by weight soybean oil, 2.00% by weight castor oil and 37.00% by weight vaseline oil. As an emulsifier, polyethylene glycol mono- or diesters are disclosed, at concentrations of ca. 10 to 12% by weight. The active ingredient used is pelargonic acid.

Document DD 236014 discloses oily cosmetic compositions which must be clear. These compositions are used, inter alia, as bath oils and cream baths. In addition to 20 to 80% oil, an aqueous anionic surfactant solution or water, these preparations contain a combination of certain hydrophobic and hydrophilic emulsifiers or non-ionic surfactants.

Document DE 44 24 210 describes cosmetic or dermatologic shower preparations having a surfactant content of at most 55% by weight, and an oil content of more than 45% by weight, wherein the preparations are essentially water-free. Owing to the high oil content, these preparations have a regenerative effect with respect to the general skin condition. At the same time, they have good foam development and high cleansing power.

EP 0867176 describes shower preparations having a high, but in comparison to the prior art, significantly lower oil content. However, a high level of refatting is achieved with improved foam performance and compatibility.

Document WO 03/051319 also discloses oily cleansing products, in this case however cleaning products based on oil-containing microemulsions. A method for preparing these oil-containing microemulsions is described. At a constant total amount of surfactant, the primary surfactant/cosurfactant ratio can be varied.

It is disclosed in document WO 2005/065629 that oil-containing, water-free surfactant preparations can be designed such that they counteract enzyme damage to the enzymes of the upper skin layers.

Document WO 2012/104025 also describes lipid-containing bath preparations, which are admixed with probiotic active ingredients.

For deeper skin freshening and cleansing, there are cleansing compositions which have an exfoliating effect. The exfoliating effect can be caused by the use of abrasive particles. The abrasive particles are, as a rule, natural or synthetic water-insoluble solids in the form of particles having an average diameter of 100 to 400 µm and a round or non-round shape.

In the course of an exfoliating treatment, the abrasive effect of the particles used can irritate the skin. In exceptional cases, especially in the case of dry and/or sensitive skin and/or aged skin, irritation can result.

In the past there has been no lack of attempts at counteracting this irritation, for example by caring additives which soothe the skin and/or by using exfoliating particles which dissolve during use and thus exhibit a decreasing exfoliating effect.

Water-soluble particles, composed of crystal-forming sugars or salts for example, can be integrated into aqueous surfactant-containing solutions which are oversaturated with these sugars or salts. However, such solutions are difficult to stabilize; the particles tend to settle.

In addition, such formulations lack refatting components which can soothe the skin and effect regeneration.

The term "sugars" can be understood as mono- and oligosaccharides (dimers to decamers of monosaccharides), which are sweet-tasting, are water-soluble and usually crystalline compounds. This is in contrast to polysaccharides, which are only poorly soluble or insoluble in water, do not have a uniform molar mass and are practically taste-free.

Such cleansing preparations are described, for example, in documents DE 102013224336 and DE 102013224368. These preparations are preparations based on water which contain no or only small amounts of lipids.

Abrasive particles may also be incorporated directly into lipid-containing preparations. A largely pasty consistency counteracts the sinking of these particles. However, such formulations, even on incorporation of amphiphilic components, lack the foam desired by the consumer.

There was, therefore, a need to provide oil-containing largely water-free cleansing compositions which achieve deeper cleansing.

Furthermore, the abrasive particles, which are added to the oil-containing largely water-free cleansing compositions, should be distributed and remain essentially stable in the preparation.

On using the preparations according to the invention, a cleansing effect comparable to customary cleansing products should be achieved. This is shown, for example, by adequate foam formation.

In order to achieve a particularly low-irritant exfoliating effect, it is particularly advantageous if the exfoliating particles predominantly dissolve during use and the exfoliating effect therefore reduces during the course of the use.

SUMMARY OF THE INVENTION

It has now been found, surprisingly, that cleansing preparations based on an oil/polyol mixture comprising abrasive particles and one or more surfactants soluble in oil are able to achieve the aforementioned object.

It is advantageous in this case, if the oil phase comprises a hardened vegetable oil or a mixture of different hardened vegetable oils and/or fats for structuring in order to improve the stability of the preparation.

It is also advantageous if the cleansing preparation also comprises polymeric structurants, particularly anionic polymers in order to effect structuring.

Cleansing preparations with abrasive effect having a water content of <5.0% by weight, preferably <1.5% by weight, particularly preferably <0.2% by weight, comprising
a. lipids
b. polyols
c. oil-soluble surfactants
d. abrasive particles and
e. polymeric structurants,
are suitable to achieve the aforementioned object.

Preference is given here to cleansing preparations having a particular ratio by weight of certain components. It is preferable if the ratio by weight of lipids to polyols is from 4:1 to 1:4. Furthermore, it is preferred that the ratio of the sum total of the parts by weight of lipids and polyols to the parts by weight of surfactants is from 2:1 to 1:2 and preferably from 1.5:1 to 1:1.5.

The cleansing preparations comprise <5.0% by weight, preferably <1.5% by weight, particularly preferably <0.2% by weight water. The water content can be determined by Karl-Fischer titration. The Karl-Fischer determination of water is suitable in order to determine the water content in organic solvents, essential oils, ointments and other organic substances. The basis of the method is the fact that iodine and sulfur dioxide only react to iodide and sulfate in the presence of water. The end point of the titration is indicated by the appearance of a yellow-brown coloring; at this point all the water is consumed and iodine no longer reacts to form colorless iodide. Today, this determination is carried out with prepared, commercially available solutions.

The cleansing preparations comprise surfactants which are soluble in oil. It has proven to be advantageous if the preparations comprise a principal surfactant which is preferably at least one non-ionic surfactant, in particular an amide of a $C_{10}$-$C_{16}$-fatty acid, particularly preferably a monoisopropylamide. Principal surfactants in the context of the present invention are those surfactants which are present in the predominant amount, taking into consideration all surfactants in the preparation according to the invention.

In addition to the prinicpal surfactant, further surfactants may be present which are referred to as cosurfactants. It is preferred if at least one cosurfactant is another amide of a $C_{10}$-$C_{16}$-fatty acid. This amide of a $C_{10}$-$C_{16}$-fatty acid is different from the amide of a $C_{10}$-$C_{16}$-fatty acid used as principal surfactant. It is particularly preferred if the cosurfactant is a diethanolamide.

It has also been found to be favorable if the cosurfactants comprise further, structurally different, non-ionic surfactants. Particularly preferred surfactants as further non-ionic surfactants are selected from the group of alkoxylated fatty alcohols having a chain length of 8 to 16, preferably 10 to 14, carbon atoms and a degree of alkoxylation of 2 to 10, preferably 2 to 6. The degree of alkoxylation describes the number of alkoxy groups in the molecule. Preferred alkoxy groups are propylene oxide and ethylene oxide. Ethylene oxide is particularly preferred. An ethylene oxide radical can be abbreviated as EO. The degree of ethoxylation is understood as the number of the EO radicals present.

It is particularly preferred if the cosurfactants comprise amides of a $C_{10}$-$C_{16}$-fatty acid and alkoxylated fatty alcohols having a chain length of 8 to 16, preferably 10 to 14, carbon atoms and a degree of alkoxylation of 2 to 10, preferably 2 to 6.

It is also possible for the cosurfactants to comprise further non-ionic surfactants.

The content of oil-soluble surfactants is 10 to 60% by weight, preferably 20 to 50% by weight, particularly preferably 25 to 40% by weight, based on the total weight of the preparation.

The lipids according to the invention consist of a mixture of lipids which are liquid and solid at room temperature. The lipids which are liquid at room temperature may be synthetic and/or natural, mineral and/or vegetable oils. It is preferred if the liquid lipids are vegetable oils, particularly preferably castor oil and/or soybean oil and/or oil from sunflower seeds.

The lipids which are solid at room temperature can be hardened vegetable oils and/or fats. Examples which may be mentioned here are hydrogenated vegetable oil, e.g. Dermofeel Viscolid from Dr. Straetmans and hydrogenated vegetable fat, e.g. VGB 22 from ADM.

The content of lipids in the preparations according to the invention is 5.5 to 12.0% by weight, based on the total weight of the preparation.

The polyol preferred according to the invention is glycerol. With the aid of the polyols, in particular glycerol, the total weight of the preparations according to the invention is brought up to 100% by weight. It is preferred if the content of polyols is in a concentration range of 5 to 40% by weight, preferably 10 to 27% by weight.

The cleansing preparations according to the invention comprise polymeric structurants which are preferably incorporated into the mixing phase of surfactant(s) and polyol(s). The structurants preferred according to the invention are anionic polymers. These anionic polymers are neutralized with a base in the course of the preparation of the cleansing preparations according to the invention. For the neutralization of the anionic polymer, an amine is preferably used, particularly preferably aminomethylpropanol.

The anionic polymer is preferably a cross-linked acrylic acid copolymer. It is further preferred if, for the synthesis of the acrylic acid copolymer, a vinyl monomer, particularly preferably a vinylpyrrolidone monomer, is used as a further monomer in addition to the acrylic acid monomer.

The content of structurants in the preparations according to the invention is 0.5 to 3.0% by weight, preferably 0.8 to 2.5% by weight, based on the total weight of the preparation.

In the cleansing preparations according to the invention, soluble and/or insoluble particles are present as solid abrasive particles.

In the context of the present invention, solid abrasive particles, which are soluble, are understood to mean particles which are present in the cleansing preparation in the solid state of matter, in particular in crystal form. When using the cleansing preparation, for example during showering, the cleansing preparation comes into contact with a relatively larger amount of water, such that the cleansing preparation is diluted. This usually leads to the gradual dissolution of the solid particles, especially crystals.

The solid abrasive particles, which are soluble, are preferably generated from sugars and/or suitable and skin-compatible salts. Particular preference is given to using sucrose and/or sodium chloride to form the soluble particles.

The solid abrasive particles which can be used according to the invention, which are insoluble, have a synthetic and/or natural origin. insoluble particles of natural origin can be of either mineral or vegetable origin.

The cleansing preparations according to the invention may comprise solid abrasive particles which are soluble or solid abrasive particles which are insoluble, and also mixtures of soluble and insoluble particles.

The present invention also relates to the use of cleansing preparations with abrasive effect having a water content of <5.0%, preferably <1.5%, particularly preferably <0.2%, comprising
  a. lipids
  b. polyols
  c. oil-soluble surfactants
  d. abrasive particles and
  e. polymeric structurants
for deep cleansing of dry and/or sensitive skin and/or aged skin.

The following surfactants may be used advantageously in the preparations according to the invention:

The amides of fatty alcohol sulfates or of fatty alcohol ether sulfates to be used favorably according to the invention have the following structure:

Here, b can have values from 0 to 10, preferably 1 to 5. $R^2$ is selected from the group of branched and unbranched alkyl groups having 6 to 24 carbon atoms.

The preferred fatty alcohol ether sulfate is MIPA-laureth sulfate.

The fatty alcohol ethoxylates to be used favorably according to the invention have the following structure:

Here, c can have values from 2 to 10, preferably 2 to 6. $R^3$ is selected from the group of branched and unbranched alkyl groups having 8 to 16 carbon atoms, particularly 10 to 14 carbon atoms.

The preferred fatty alcohol ethoxylate is laureth-4.

Advantageously, the fatty acid mono- or diethanolamides to be used favorably according to the invention have the following structures:

$R^4$ and $R^5$ are selected from the group of branched and unbranched alkyl groups and/or alkenyl groups having 6 to 24 carbon atoms, particularly 10 to 16 carbon atoms.

The preferred fatty acid diethanolamide is coconut fatty acid diethanolamide (cocamide DEA). Natural coconut fatty acid comprises as essential constituents lauric acid to 44-51% by weight, myristic acid to 13-18% by weight, palmitic acid to 8-10% by weight, caprylic acid to 6-9% by weight, capric acid to 6-10% by weight, oleic acid to 5-8% by weight, stearic acid to 1-3% by weight, linoleic acid to 0-2% by weight and caproic acid to 0-1% by weight.

Very particular preference is given to using mixtures of MIPA-laureth sulfate, laureth-4 and coconut fatty acid diethanolamide. Such mixtures are obtainable, for example, under the name ZETESOL® 100 from Zschimmer & Schwarz Chemische Fabriken, Lahnstein/Rhein, or TEXAPON® WW 99 from Henkel KGaA, Düsseldorf.

The oils according to the invention are preferably selected from the group of triglycerides of the following structure:

Where $R^6$, $R^7$ and $R^8$ are mutually independently selected from the group of branched and unbranched alkylcarboxyl or alkenylcarboxyl groups having 12 to 24 carbon atoms. It is advantageous, if appropriate, if one or more aliphatic hydrogen atoms of the alkylcarboxyl or alkenylcarboxyl groups are substituted by hydroxyl groups.

To select the lipids that are liquid at room temperature it is particularly advantageous if $R^6$, $R^7$ and/or $R^8$ have 16 to 20 carbon atoms and are selected from the group of mono- to tri-unsaturated carboxylic acid radicals.

If $R^6$, $R^7$ and/or $R^8$ bear hydroxyl groups, the preferred alkenylcarboxyl radical is the ricinoleic acid radical.

It is particularly advantageous to select the lipids according to the invention that are liquid at room temperature from the group of soybean oil, castor oil and sunflower seed oil.

To select the lipids that are solid at room temperature, it is advantageous if these have a melting point or melting range within a window of 50 to 70° C., an iodine number between 0 and 5 and a free fatty acids content of 0 to 0.8% by weight.

In the context of the present invention, polyols are polyhydric alcohols. They are low molecular weight compounds having at least two hydroxyl groups.

The compounds propylene glycol and glycerol are the preferred compounds in accordance with the invention, glycerol being particularly preferred.

In the context of the present invention, solid abrasive particles are soluble and/or insoluble particles which create an exfoliating effect.

In the soluble particles, the exfoliating effect is created by the undissolved proportion of sugars or salts which may be present in crystalline form. This is achieved by a high sugar and/or salt concentration such that not all sugar and/or salt molecules can dissolve in the preparation according to the invention and are present in solid or crystalline form. These exfoliating substances of this kind come into contact with water when used during the showering or washing process, for example, when showering off or washing off the foam and the cleansing preparation at the end of the cleansing process. As a result, dissolution of the sugar and/or salt crystals is ensured, which leads to a decreasing exfoliating effect. At the same time, however, this also results in no, or practically no residues of the exfoliating substances in sinks or treatment devices. Practically no residues means that, in a few individual cases, exceptionally low traces of the cleansing preparation after the washing process are visible on wash basins or application facilities, but which are removable in a simple manner by rinsing or wiping off.

The sugar which may be used in accordance with the invention may be, for example, mono-, di- or oligosaccharides. Mono- or disaccharides may be, for example, sucrose, glucose or fructose, where sucrose is especially preferred.

The salts in the preparations according to the invention should be compatible with skin and suitable in the medium of the cleansing preparations to form solid structures, preferably crystals. These may be, for example, alkali metal salts such as sodium chloride, potassium chloride, sodium sulfate and/or potassium sulfate, where sodium chloride is especially preferred. The salts in the preparations according to the invention may also be alkaline earth metal salts, such as magnesium chloride and/or magnesium sulfate, for example.

The insoluble exfoliating agents may be selected advantageously, for example, from the group of polyethylene, clay, sand, plastic particles, crushed or ground grains of walnut shells, apricot, peach and/or almond kernels.

The polymeric structurants which may be used in accordance with the invention are anionic polymers. Anionic polymers can be polymers having, for example, acrylic acid as monomer. Usable in accordance with the invention are, for example, polyacrylates such as acrylate-alkyl acrylate copolymers, particularly those which are selected from the group of so-called carbomers.

In the synthesis of the anionic polymers in accordance with the invention, particular preference is given to additionally using vinyl monomers, vinylpyrrolidone being particularly preferred.

Particularly preferred in accordance with the invention are compounds with the INCI name Acrylic acid/VP Crosspolymer.

BRIEF DESCRIPTION OF THE DRAWINGS

In the accompanying drawings.

DETAILED DESCRIPTION OF EMBODIMENTS OF THE INVENTION

In order to demonstrate the efficacy of the preparations according to the invention, a selected preparation, OELPEEL:70, was used in an in-use-screening. The preparation OELPEEL:70 was distributed to 100 female volunteers who had to use the product at least four times within a period of 12 days. A questionnaire was handed out with which various product benefits were polled. Of 100 questionnaires, 83 were returned and could be evaluated. The volunteers were all female, and on average 37.08 years old. All volunteers were users of shower exfoliating products. The questions could be answered on a scale of 1 (don't agree) to 7 (agree). The responses were evaluated in relation to the determination of the respective averages of the absolute and relative frequency. In addition, so-called top-boxes and low-boxes were determined, i.e. the responses were grouped in relation to the best and second best and the weakest and second weakest statements respectively.

Figure 1:
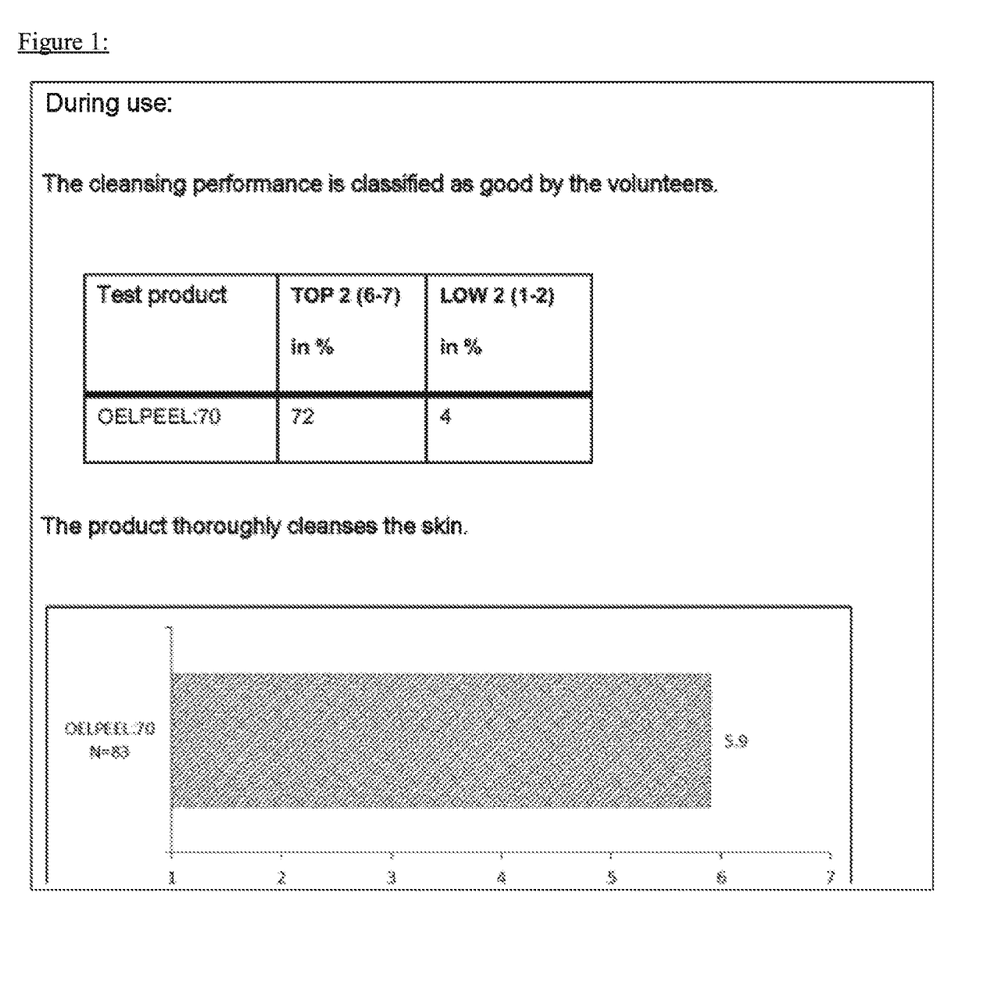
FIG. 1 shows the rating of a product according to the present invention by a panel of volunteers with respect to the product's performance regarding cleansing of the skin.

The cleansing performance of the OELPEEL:70 preparation was assessed during use and 36.4% of the volunteers were in agreement, specifically with the highest possible value of 7 (see FIG. 1). The cleansing performance of OELPEEL:70 is overall exceptionally well rated.

Figure 2:
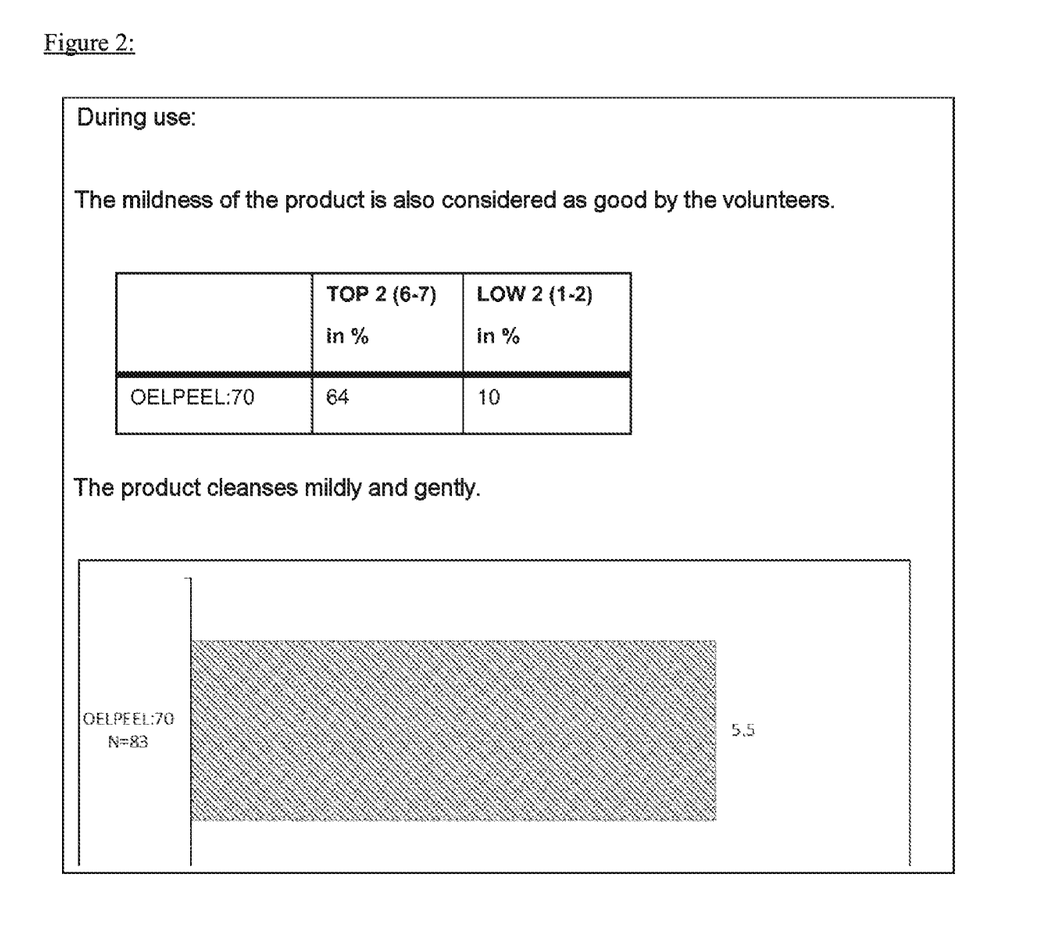
FIG. 2 shows the rating of the product according to the present invention by a panel of volunteers with respect to the product's mildness.
Figure 3:
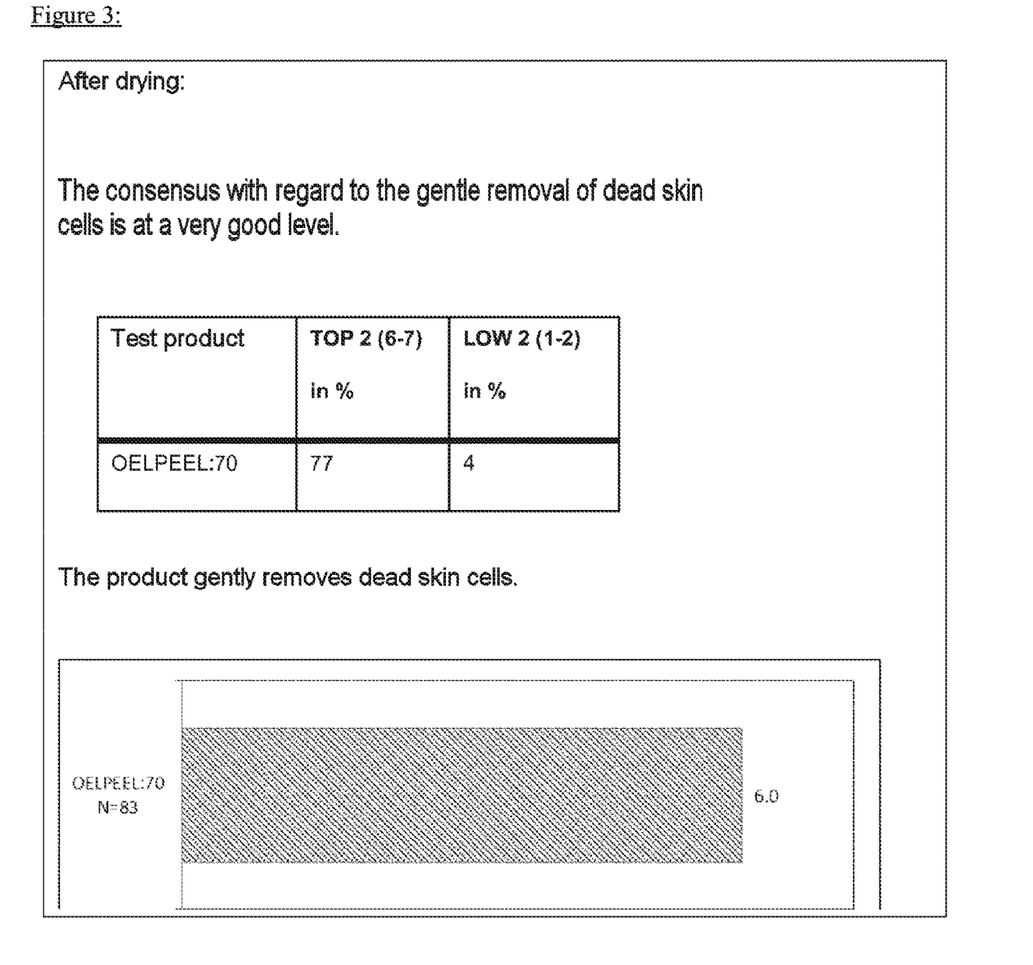
FIG. 3 shows the rating of the product according to the present invention by a panel of volunteers with respect to the product's performance regarding the removal of dead skin.
Figure 4:
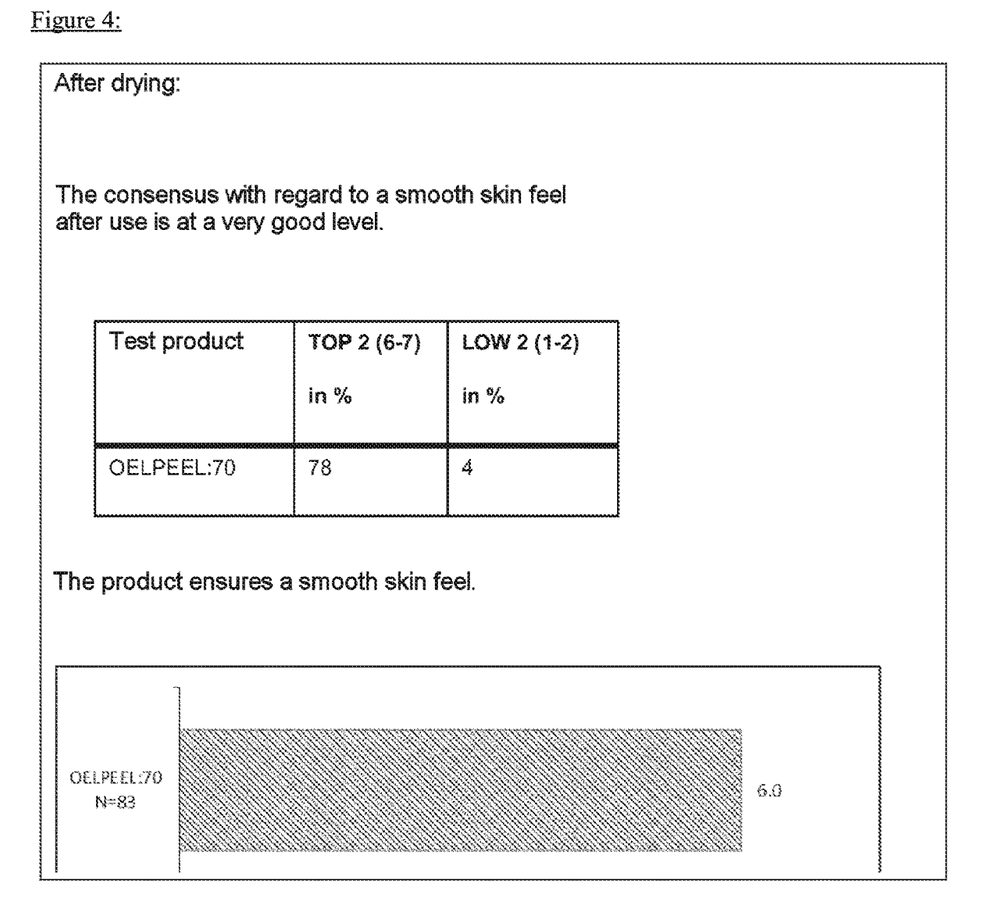
FIG. 4 shows the rating of the product according to the present invention by a panel of volunteers with respect to the product's performance regarding smooth skin feel.

The mildness was also assessed during use and 28.7% of the volunteers rated the mildness with the highest possible value of 7 and 32.2% with a value of 6, the second highest possible value. The OELPEEL:70 preparation has an excellent mildness; see FIG. 2.

After drying, the volunteers had to give an assessment of the gentle removal of skin cells, of the skin feel and of the dryness of the skin, (see FIGS. 3 to 6). 47.2% of the volunteers rated the removal of skin cells with the highest value of 7. It follows from this that the exfoliating effect of the sugar crystals was rated as very good.

Figure 5:
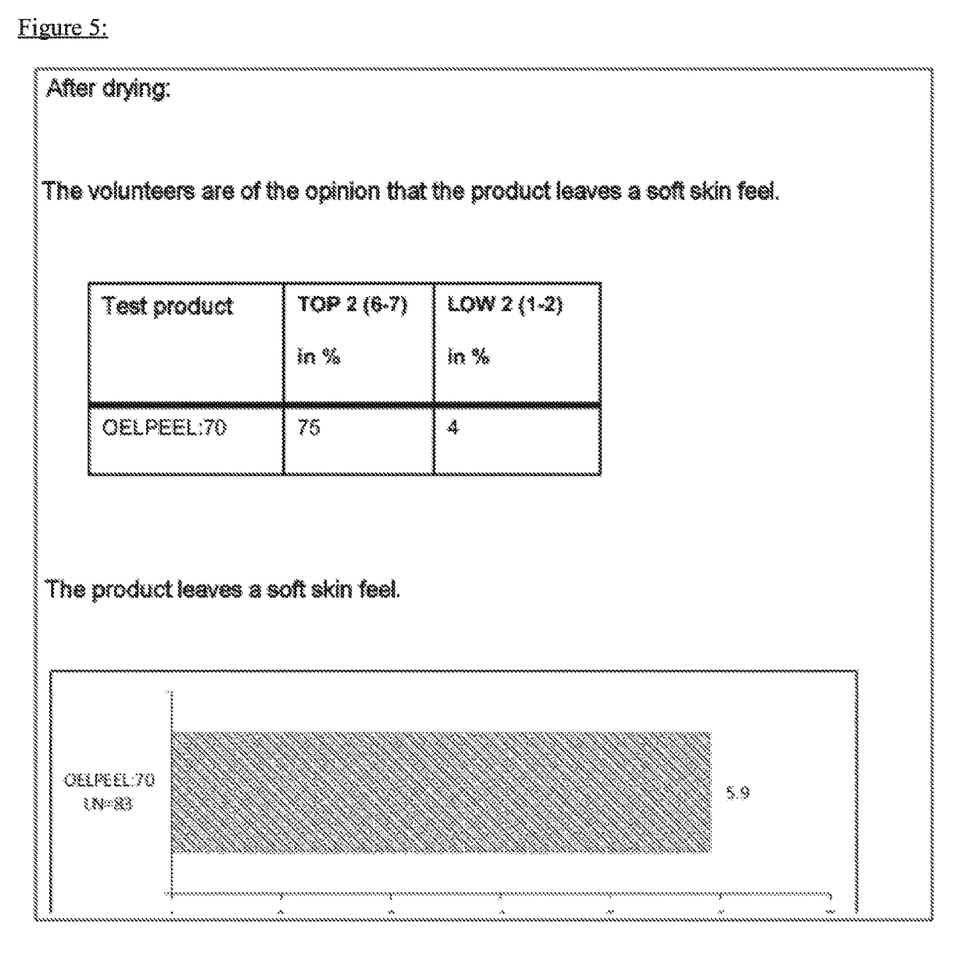
FIG. 5 shows the rating of the product according to the present invention by a panel of volunteers with respect to the product's performance regarding soft skin feel.

The skin feel with respect to smoothness and softness is excellent, likewise being rated with high values (FIG. 5).

Figure 6:
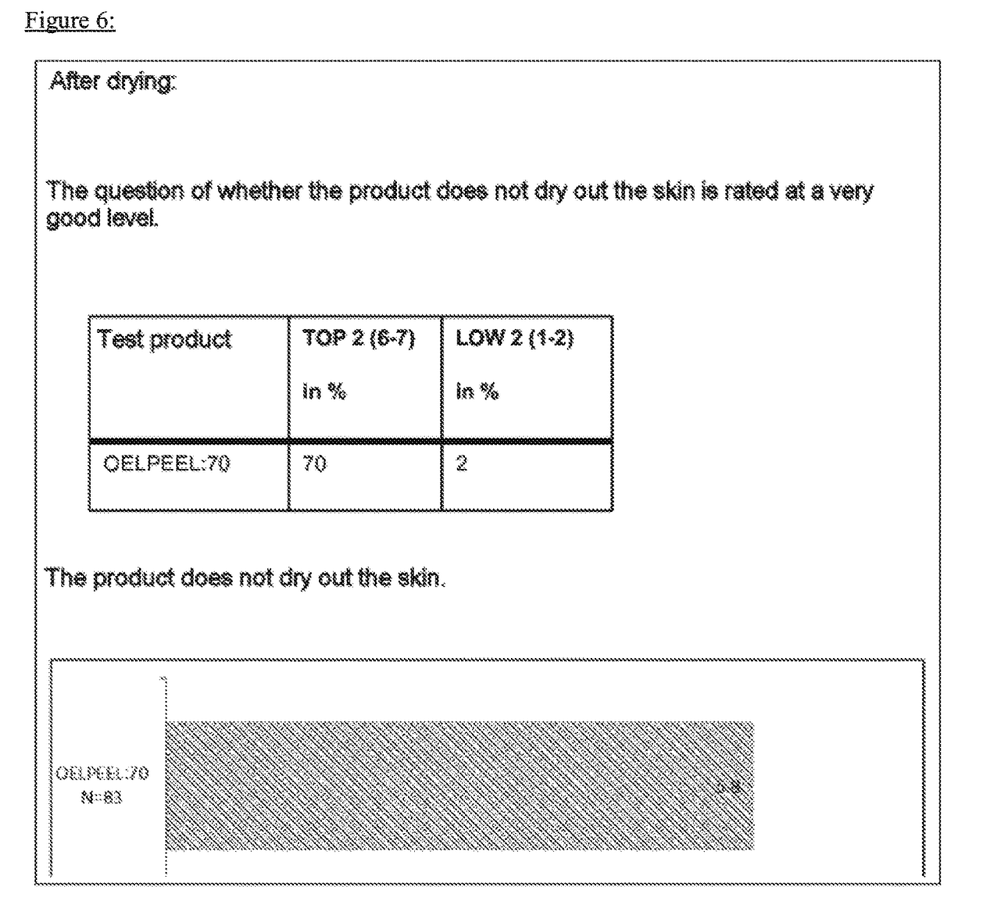
FIG. 6 shows the rating of the product according to the present invention by a panel of volunteers with respect to the product's performance regarding drying out of the skin.

34.1% of the volunteers agreed with the highest value that the product does not dry out the skin (FIG. 6).

Figure 7:
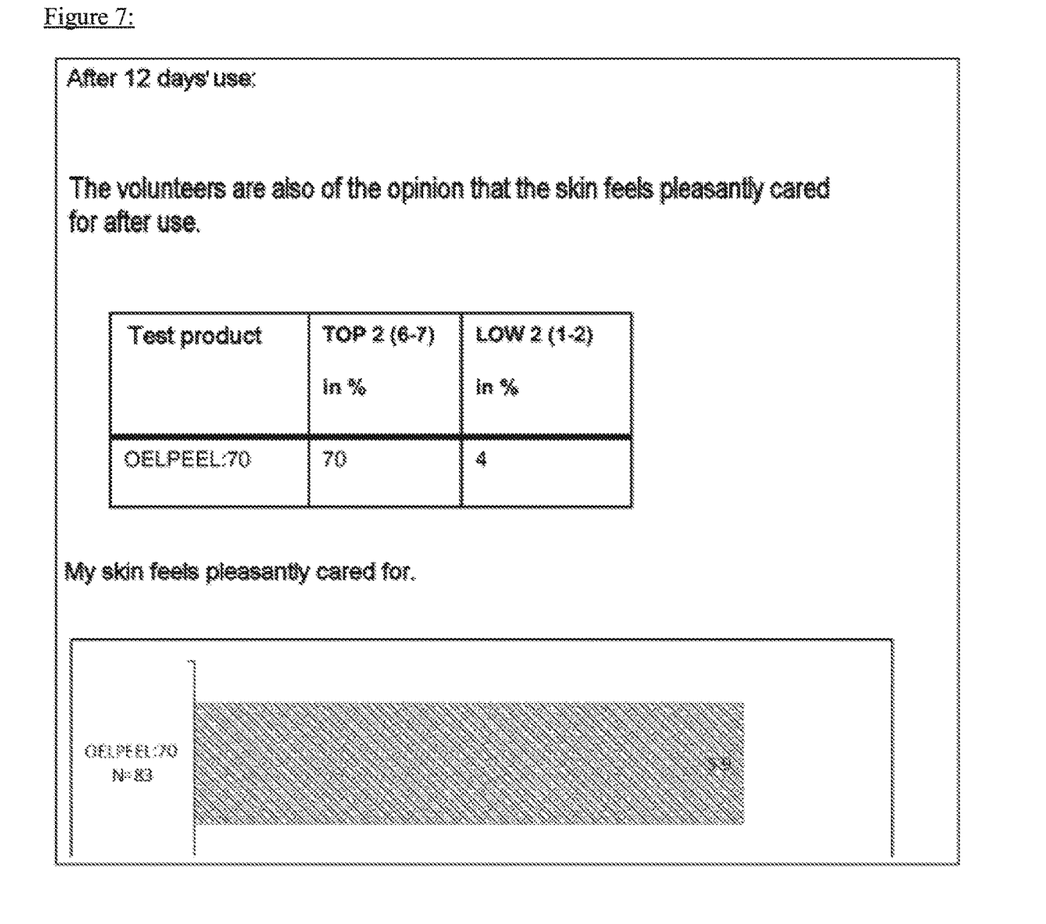
FIG. 7 shows the rating of the product according to the present invention by a panel of volunteers with respect to the product's performance regarding pleasant skin care.
Figure 8:
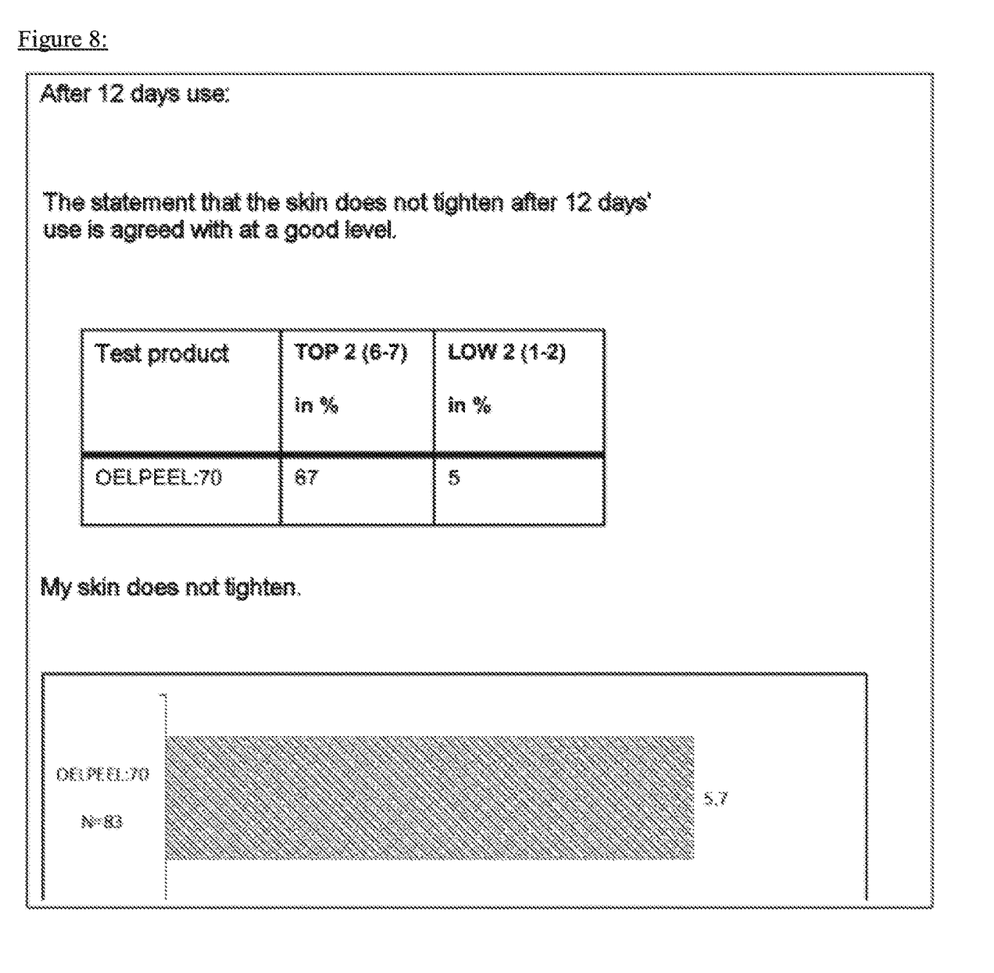
FIG. 8 shows the rating of the product according to the present invention by a panel of volunteers with respect to the product's performance regarding tightening of the skin.
Figure 9:
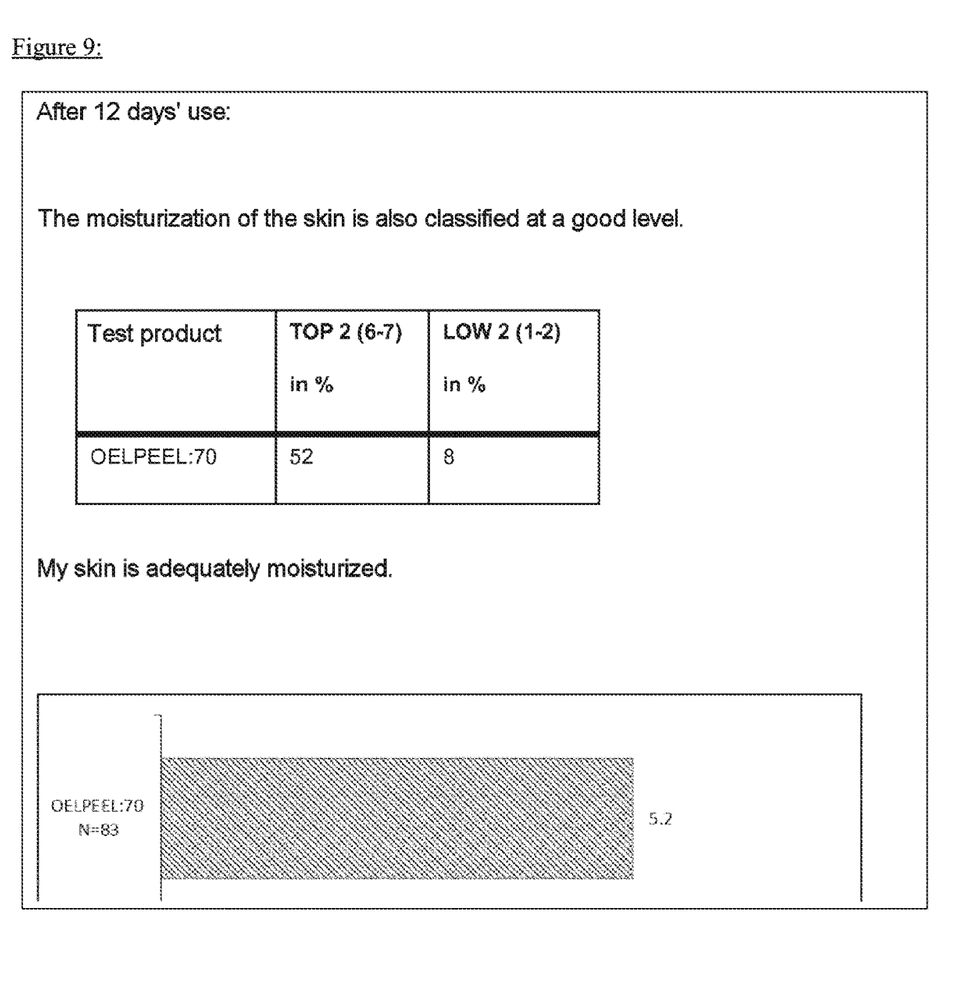
FIG. 9 shows the rating of the product according to the present invention by a panel of volunteers with respect to the product's performance regarding miniaturization of the skin.

After 12 days' use, the volunteers were questioned on the care, on the tenderness of the skin and on the moisturization of the skin, see FIGS. 7 to 9. All three aspects were rated as above average by the volunteers.

The product used in the in-use-screening, OELPEEL:70, has the following composition:

| INCI | Trade name Manufacturer | |
|---|---|---|
| Acrylic acid/VP Crosspolymer | Ultrathix P-100 Ashland | 1.1 |
| MIPA Laureth Sulfate + Laureth-4 + Cocoamide DEA | Zetesol 100 Zschimmer & Schwarz | 35.0 |
| Glycerine + Aqua | Glycerine 99.5% BP Emery Oleochemicals | to 100% |
| Aminomethyl Propanel + Aqua | AMP 95 Angus Chemie | 0.3 |
| Ricinus Communis Seed Oil | Rizinusoel Gustav Heess | 5.0 |
| Glycine Soja Oil + Ricinus Communis Seed Oil + Propyl Gallate | Sojaöl Gustav Heess | 5.0 |
| BHT | Ionol CP; Cat. No. 1240 Oxiris Chemicals | 0.05 |
| Sucrose | Sandzucker Nordzucker AG | 30.0 |
| Hydrated Silica | Sipernat 2200 Evonik Industries | 5.0 |
| Hydrogenated Vegetable Oil | Dermofeel Viscolid Dr. Straetmanns | 1.0 |
| Fragrance | Parfum | 1.0 |

EXAMPLES

All figures in the present application are figures in % by weight, unless other units are expressly stated.

The figures in the examples below specify the raw material contents. These correspond to the active content unless the relevant percentage active content is specified in the trade name.

| INCI | Trade name Manufacturer | 1 | 2 | 3 | 4 | 5 |
|---|---|---|---|---|---|---|
| Acrylic acid/VP Crosspolymer | Ultrathix P-100 Ashland | 1.2 | 1.3 | 1.0 | 1.5 | 1.3 |
| MIPA Laureth Sulfate + Laureth-4 + Cocoamide Dea | Zetesol 100 Zschimmer & Schwarz | 25.5 | 30.0 | 35.0 | 30.0 | 40.0 |
| Glycerine + Aqua | Glycerine 99.5% BP EmeryOleochemicals | to 100% | to 100% | to 100% | to 100% | to 100% |
| Aminomethyl Propanol + Aqua | AMP 95 Angus Chemie | 0.25 | 0.3 | 0.3 | 0.2 | 0.25 |
| Ricinus Communis Seed Oil | Rizinusoel Cat. No. 300031 Gustav Hess | 5.0 | 5.0 | 4.5 | 2.5 | 3.0 |
| Helianthus Annuus Seed Oil | Sonnenblumenoel raff. Henry Lamotte | 3.0 | 5.0 | 5.0 | 5.0 | 1.0 |
| BHT | Ionol CP; Cat. No. 1240 Oxiris Chemicals | 0.05 | 0.06 | 0.05 | 0.04 | 0.00 |
| Sucrose | Sandzucker Nordzucker AG | 35.0 | 30.0 | 30.0 | 20.0 | 25.0 |
| Hydrated Silica | Sipemat 2200 Evonik Industries | 6.0 | 4.0 | 4.7 | 8.0 | 3.5 |
| Propylene Glycol | Propylene Glycol USP/EP-RMT Dow Chemical | 0.0 | 2.0 | 0.0 | 5.0 | 0.0 |
| Hydrogenated Vegetable Oil | Dermofeel Viscolid Dr. Straetmans | 0 | 0.5 | 1.2 | 0.7 | 0 |
| Hydrogenated Vegetable Fat | VGB 22 ADM | 1.5 | 0.5 | 0 | 0.6 | 1.9 |
| Fragrance | Parfum | 1 | 1.1 | 1.0 | 1.2 | 1.0 |

What is claimed is:

1. A skin cleansing preparation, wherein the preparation has an abrasive effect, comprises less than 5% of water and comprises
   (a) one or more lipids,
   (b) one or more polyols,
   (c) one or more oil-soluble surfactants,
   (d) one or more kinds of abrasive particles, and
   (e) one or more polymeric structurants.

2. The preparation of claim 1, wherein a weight ratio of (a) to (b) is from 4:1 to 1:4.

3. The preparation of claim 1, wherein a weight ratio of (a) plus (b) to surfactants is from 2:1 to 1:2.

4. The preparation of claim 1, wherein (c) comprises one or more non-ionic surfactants.

5. The preparation of claim 1, wherein the preparation comprises at least one non-ionic principal surfactant.

6. The preparation of claim 1, wherein the preparation comprises at least one cosurfactant.

7. The preparation of claim 6, wherein the cosurfactant is an amide of a $C_{10}$-$C_{16}$-fatty acid.

8. The preparation of claim 6, wherein the cosurfactant is an amide of a $C_{10}$-$C_{16}$-fatty acid which is different from a principal surfactant.

9. The preparation of claim 6, wherein the cosurfactant is selected from alkoxylated fatty alcohols having a chain length of from 8 to 16 and a degree of alkoxylation of from 2 to 10.

10. The preparation of claim 6, wherein the cosurfactant is selected from ethoxylated fatty alcohols.

11. The preparation of claim 6, wherein the cosurfactant comprises an amide of a $C_{10}$-$C_{16}$-fatty acid and an alkoxylated fatty alcohol having a chain length of from 8 to 16 and a degree of alkoxylation of from 2 to 10.

12. The preparation of claim 1, wherein (b) comprises at least one of propylene glycol and glycerol.

13. The preparation of claim 1, wherein (e) comprises one or more anionic polymers.

14. The preparation of claim 1, wherein (e) comprises one or more crosslinked acrylic acid copolymers.

15. The preparation of claim 1, wherein (d) comprises one or more water-soluble kinds of particles.

16. The preparation of claim 15, wherein the one or more water-soluble kinds of particles comprise sugar and/or salt particles.

17. The preparation of claim 16, wherein (d) comprises sucrose.

18. The preparation of claim 1, wherein (d) comprises sodium chloride.

19. The preparation of claim 1, wherein (d) comprises particles of natural origin.

20. A skin cleansing preparation, wherein the preparation has an abrasive effect, comprises less than 1.5% of water and comprises
　　(a) one or more lipids,
　　(b) one or more polyols,
　　(c) one or more oil-soluble surfactants,
　　(d) one or more kinds of abrasive particles, and
　　(e) one or more polymeric structurants,
　　wherein a weight ratio of (a) to (b) is from 4:1 to 1:4,
　　wherein (b) comprises at least one of propylene glycol and glycerol,
　　wherein (e) comprises one or more crosslinked acrylic acid copolymers.

* * * * *